United States Patent
Kawa et al.

(10) Patent No.: US 7,179,880 B2
(45) Date of Patent: Feb. 20, 2007

(54) COSMETIC PREPARATION CONTAINING POLYCARBONATES

(75) Inventors: Rolf Kawa, Monheim (DE); Lars Zander, Duesseldorf (DE); Alfred Westfechtel, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/495,391

(22) PCT Filed: Nov. 6, 2002

(86) PCT No.: PCT/EP02/12373

§ 371 (c)(1),
(2), (4) Date: May 13, 2004

(87) PCT Pub. No.: WO03/041676

PCT Pub. Date: May 22, 2003

(65) Prior Publication Data

US 2005/0090637 A1   Apr. 28, 2005

(30) Foreign Application Priority Data

Nov. 14, 2001 (DE) ............... 101 55 769

(51) Int. Cl.
*C08G 64/00* (2006.01)
(52) U.S. Cl. ............... 528/196; 424/400; 424/401; 514/938
(58) Field of Classification Search ........... 424/400, 424/401; 514/938; 528/196, 198
See application file for complete search history.

(56) References Cited

U.S. PATENT DOCUMENTS

| | | | |
|---|---|---|---|
| 2,347,562 A | | 4/1944 | Johnston |
| 5,387,354 A | * | 2/1995 | Mizui et al. ............ 508/462 |
| 5,556,628 A | | 9/1996 | Derian et al. |
| 5,621,065 A | * | 4/1997 | Pudleiner et al. ......... 528/84 |
| 5,705,169 A | | 1/1998 | Stein et al. |
| 5,730,960 A | | 3/1998 | Stein et al. |
| 5,945,091 A | | 8/1999 | Habeck et al. |
| 6,159,454 A | | 12/2000 | Schuhmacher et al. |
| 6,193,960 B1 | | 2/2001 | Metzger et al. |
| 6,482,418 B1 | | 11/2002 | Loehl et al. |
| 6,566,563 B1 | | 5/2003 | Westfechtel et al. |
| 6,592,883 B1 | * | 7/2003 | Gers-Barlag et al. ...... 424/401 |
| 2001/0022965 A1 | | 9/2001 | Heger et al. |
| 2002/0107334 A1 | * | 8/2002 | Krishnan et al. .......... 525/413 |

FOREIGN PATENT DOCUMENTS

| | | |
|---|---|---|
| DE | 1 768 313 | 4/1971 |
| DE | 195 13 164 | 10/1996 |
| DE | 195 25 406 | 1/1997 |
| DE | 197 12 033 A1 | 9/1998 |
| EP | 0 586 275 | 3/1994 |
| EP | 0 693 471 B1 | 1/1996 |
| EP | 0 694 521 B1 | 1/1998 |
| EP | 0 818 450 A1 | 1/1998 |
| EP | 0 998 900 | 5/2000 |
| EP | 1 077 058 | 2/2001 |
| EP | 1 127 567 | 8/2001 |
| JP | 11181333 * | 1/2001 |
| WO | WO 00/01755 | 1/2000 |

OTHER PUBLICATIONS

Translation of JP 11181333; Production of Polycarbonate Jan. 16, 2001, Takizawa et al.*
Römpp Chemie Lexikon—Version 1.0, Stuttgart/New York: Georg Thieme Verlag 1995 (p2, I. 30-p3. I.3).
Kirk-Othmer, Encyclopedia of Chemical Technology, 3rd Edition, 1979, vol. 8, pp. 900-915.
P.Finkel, "Formulierung kosmetischer Sonnenschutzmittel", SÖFW-Journal, 122, (1996), pp. 543-546, and 548.
P.Finkel, "Formulierung kosmetischer Sonnenschutzmittel", Parfümerie und Kosmetik,80.(1999).pp. 10-12,14-16.
Lochhead et al., "Encyclopedia of Polymers and Thickeners", Cosmetics & Toiletries, vol. 108,(1993), pp. 95-135.
Kosmetikverordnung, Appendix 6, Parts A and B.
"Kosmetische Färbemittel", Farbstoffkommission der Deutschen Forschungsgemeinschaft, Verlag Chemie, Weinheim, (1984), pp. 81-106.
DIN 53 240, Q-C 1220.0, Methoden der Analyse in der Chemie, vol. 4, p. 322.
Hecht et al., "Methoden der Analyse in der Chemie," Akademische Verlagsgesellschaft, vol. 4, p. 322.

* cited by examiner

Primary Examiner—Terressa Boykin
(74) Attorney, Agent, or Firm—John F. Daniels; Daniel S. Ortiz

(57) ABSTRACT

A cosmetic and/or pharmaceutical composition containing: (a) a polycarbonate having a molecular weight of from about 300 to 100,000; (b) optionally, an oil component; (c) optionally, an emulsifier; and (d) optionally, water.

19 Claims, No Drawings

COSMETIC PREPARATION CONTAINING POLYCARBONATES

BACKGROUND OF THE INVENTION

This application is a 371 of PCT/EP02/12373 filed Nov. 6, 2002.

FIELD OF THE INVENTION

This invention relates to cosmetic and/or pharmaceutical emulsions containing special polycarbonates and to the use of these polycarbonates in cosmetic/pharmaceutical preparations in general and in sun protection preparations in particular for improving the water resistance of these preparations.

Although emulsions have been known for some time, intensive efforts are constantly being made on the cosmetic market to improve both the stability and the sensory properties of these disperse systems. Present trends include inter alia the search for new oil components and polymers which may readily be incorporated in emulsions, which allow the formulation of particularly storage-stable emulsions and which, in sensory terms, leave the skin feeling lighter.

The water resistance of the preparations is another key factor for special applications, for example sun protection products, because the UV filters are intended to remain on the skin for as long as possible without being washed off during bathing. The water resistance of a sun protection formulation is normally achieved by the addition of polymers, for example PVP/Hexadecene Copolymer (Antaron® V-216). Unfortunately, these polymers have the disadvantage that the water resistance they provide is short-lived and long-term resistance, as required for example in watersports (surfing) and in sun protection for children, cannot be achieved. In addition, the sensory properties of the emulsion in terms of absorption, spreadability and tackiness are seriously affected.

Accordingly, the problem addressed by the present invention was to provide emulsions based on new polymers which would provide the emulsions with improved sensory properties, more particularly in regard to absorption, spreadability and tackiness. Another problem addressed by the invention was to develop formulations which, compared with the prior art, would show improved water resistance, i.e. would afford improved long-term protection where UV filters are present in the formulations.

DESCRIPTION OF THE INVENTION

It has now surprisingly been found that cosmetic preparations based on special polycarbonates have improved sensory behavior in regard to spreadability, absorption and tackiness. The polycarbonates can readily be incorporated in emulsions and provide the preparations according to the invention with improved water resistance.

Accordingly, the present invention relates to cosmetic and/or pharmaceutical preparations containing polycarbonates with an average molecular weight of 300 to 100,000 and preferably in the range from 500 to 50,000. The molecular weights can be determined by gel permeation chromatography. The present invention also relates to the use of these polycarbonates in cosmetic and/or pharmaceutical preparations, more particularly for improving the water resistance of the resulting preparations. This is of major interest for sun protection formulations in particular, but is also relevant to many other types of decorative cosmetics, such as for example mascara, eye shadow, waterproof make-up, eyeliner, kajal sticks, etc.

Polycarbonates

In formal terms, polycarbonates may be regarded as polyesters of carbonic acid and diols corresponding to general formula (I):

They are obtained from polycondensation and transesterification reactions by reaction of diols with phosgene or carbonic acid diesters (CD Römpp Chemie Lexikon—Version 1.0, Stuttgart/New York: Georg Thieme Verlag 1995).

The diol component may be selected from saturated or unsaturated, branched or unbranched aliphatic dihydroxy compounds containing 2 to 30 carbon atoms or aromatic dihydroxy compounds such as, for example, glycol, propane-1,2- and -1,3-diol, butane-1,3- and -1,4-diol, pentane-1,5-diol, hexane-1,6-diol, diethylene glycol, dipropylene glycol, neopentyl glycol, bis-(hydroxymethyl)-cyclohexane, bisphenol A, dimer diols, hydrogenated dimer diols or even mixtures of the diols mentioned. Hydroxy-terminated polyethers, such as polyethylene glycols or polytetrahydrofurans for example, may also be used. In addition, polyhydric alcohols, for example glycerol, di- and polyglycerol, trimethylolpropane, pentaerythritol or sorbitol, may also be used in the polymerization.

The reaction leading to polycarbonates suitable for use in accordance with the invention is normally carried out with carbonic acid dimethyl ester and carbonic acid diethyl ester.

Polycarbonates with an average molecular weight of 300 to 100,000 are suitable for the purposes of the invention. Polycarbonates with an average molecular weight of 500 to 50,000, more particularly 500 to 20,000, are particularly suitable, polycarbonates with an average molecular weight of 1,000 to 5,000 being particularly preferred. Although polycarbonates such as these are normally a viscous or tacky material, they are easy to incorporate and, besides sensory advantages, such as reduced tackiness, provide the preparations according to the invention with improved water resistance (vide infra).

The preparations according to the invention preferably contain polycarbonates obtained by reaction of a dimer diol or α,ω-alkanediol with dimethyl or diethyl carbonate. Polycarbonates based on dimer diols and their production are known, for example, from U.S. Pat. No. 5,621,065, DE 195 25 406, DE 195 13 164 and WO 00/01755. Dimer diols are mixtures from their production. Their production is well-known from the prior art, for example from DE 1 768 313 and U.S. Pat. No. 2,347,562. Preferred dimer diol components for the reaction leading to the polycarbonates usable in accordance with the invention are dimer diols containing a total of 12 to 100 carbon atoms. $C_{12-40}$ dimer diols are particularly suitable, $C_{12-24}$ dimer diols are preferred and $C_{16-22}$ dimer diols are particularly preferred, the chain lengths mentioned here relating to one chain. Preparations based on polycarbonates obtained by reaction of hydrogenated dimer diols with iodine values of 20 to 80 and preferably 50 to 70 with dimethyl or diethyl carbonate are preferred for the purposes of the invention. According to the invention, the use of Pripol® 2033 (Uniqema), Speziol® 36/2 (Cognis Deutschland GmbH) and Sovermol® 650 NS (Cognis Deutschland GmbH) is particularly preferred for the reaction leading to the polycarbonates.

$C_{2-18}$ diols, for example decane-1,10-diol and dodecane-1,12-diol, are preferably used as the α,ω-alkanediol component. According to the invention, alkane-$C_{2-8}$-diols, more particularly alkane-$C_{2-6}$-diols, are suitable as the α,ω-alkanediol component, α,ω-pentanediol or α,ω-hexanediol being particularly preferred as the α,ω-alkanediol component for the reaction.

The polycarbonates are normally used in quantities of 0.1 to 20% by weight, preferably in quantities of 1 to 10% by weight and more particularly in quantities of 1 to 5% by weight, based on the final formulation of the cosmetic preparation.

Cosmetic and/or Pharmaceutical Preparations

The preparations according to the invention may be formulated as substantially water-free oils, creams, gels, lotions, alcoholic and aqueous/alcoholic solutions, emulsions, sprayable emulsions, wax/fat compounds, stick preparations and the like. Accordingly, the compositions according to the invention have viscosities varying from 100 to 1,000,000 mPa.s (Brookfield RVF, 23° C., spindle and r.p.m. dependent on viscosity according to the manufacturer). The preparations according to the invention preferably have a viscosity of 100 to 300,000 mPa.s at 23° C. Depending on the particular application, the preparations according to the invention contain other auxiliaries and additives, such as for example oil components, emulsifiers, surfactants, pearlizing waxes, consistency factors, thickeners, superfatting agents, stabilizers, polymers, silicone compounds, fats, waxes, lecithins, phospholipids, biogenic agents, UV protection factors, antioxidants, deodorizers, antiperspirants, antidandruff agents, film formers, swelling agents, insect repellents, self-tanning agents, tyrosine inhibitors (depigmenting agents), hydrotropes, solubilizers, preservatives, perfume oils, dyes and the like.

Oil Components

The preparations according to the invention preferably also contain at least one oil component. Oil components in the context of the invention are substances which are liquid at 20° C. and immiscible with water at 25° C. or mixtures of such substances. The combination with oil components enables the sensory properties of the preparations to be optimized. The quantity of oil components in the composition as a whole can vary between 1 and 98% by weight according to the particular formulation (for example oil, cream, lotion, sprayable emulsion). In a preferred embodiment, the preparations according to the invention contain 1 to 30% by weight oil components and more particularly 5 to 30% by weight oil components.

Suitable oil components are, for example, Guerbet alcohols based on fatty alcohols containing 6 to 18 and preferably 8 to 10 carbon atoms (for example Eutanol® G), esters of linear $C_{6-22}$ fatty acids with linear or branched $C_{6-22}$ fatty alcohols, esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{3-38}$ alkylhydroxycarboxylic acids with linear or branched $C_{6-22}$ fatty alcohols, more especially diethylhexyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di-and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols Hydagen® HSP, Sovermol® 750, Sovermol® 1102), silicone oils (cyclomethicone, silicon methicone types, etc.) and/or aliphatic or naphthenic hydrocarbons, for example mineral oil, vaseline, petrolatum, squalane, squalene or dialkyl cyclohexanes.

A distinct improvement in the sensory properties of the compositions according to the invention is achieved when dialkyl ethers and/or dialkyl carbonates are used as oil components either on their own or in conjunction with other oil components. According to the invention, therefore, dialkyl ethers and/or dialkyl carbonates are preferred oil components. In addition, silicone compounds may advantageously be used to prevent the unwanted so-called "white residues" (microfoam formation) in cosmetic formulations. For example, cyclomethicone and dimethicone are used in quantities of 1 to 20% by weight, based on the composition as a whole, for this purpose.

Surfactants/Emulsifiers

In another preferred embodiment, the preparations according to the invention additionally contain at least one emulsifier. The addition of emulsifiers improves the incorporation of the polycarbonates.

Nonionic emulsifiers are preferred for the purposes of the invention. Nonionic emulsifiers are distinguished by their kindness to the skin, their mildness and their ecotoxicologically favorable properties. In addition, the stability and sensory properties of the compositions according to the invention can be improved by the use of a combination of nonionic w/o and o/w emulsifiers. A particularly preferred combination is commercially available as Eumulgin® VL 75 (Cognis Deutschland GmbH). The compositions according to the invention contain the emulsifier(s) in a quantity of typically 0.1 to 15% by weight, preferably 1 to 10% by weight and more particularly 3 to 10% by weight, based on the total weight of the composition.

Nonionic Emulsifiers

The group of nonionic emulsifiers include:

(1) products of the addition of 2 to 50 mol ethylene oxide and/or 0 to 20 mol propylene oxide onto linear $C_{8-40}$ fatty alcohols, onto $C_{12-40}$ fatty acids and onto alkyl phenols containing 8 to 15 carbon atoms in the alkyl group;
(2) $C_{12/18}$ fatty acid mono- and diesters of addition products of 1 to 50 mol ethylene oxide into glycerol;
(3) glycerol mono- and dieters and sorbitan mono- and diesters of saturated and unsaturated $C_{6-22}$ fatty acids and ethylene oxide addition products thereof;
(4) alkyl mono- and oligoglycosides containing 8 to 22 carbon atoms in the alkyl group and ethoxylated analogs thereof;
(5) addition products of 7 to 60 mol ethylene oxide onto castor oil and/or hydrogenated castor oil;
(6) polyol esters and, in particular, polyglycerol esters such as, for example, polypolypoly-12-hydroxystearate, polyglycerol poly-ricinoleate, polyglycerol diisostearate or polyglycerol dimerate. Mixtures of compounds from several of these classes are also suitable;
(7) products of the addition of 2 to 15 mol ethylene oxide onto castor oil and/or hydrogenated castor oil;
(8) partial esters based on linear, branched, unsaturated or saturated $C_{6-22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) or mixed esters such as, for example, glyceryl stearate citrate and glyceryl stearate lactate;
(9) wool wax alcohols;
(10) polysiloxane/polyalkyl polyether copolymers and corresponding derivatives;
(11) mixed esters of pentaerythritol, fatty acids, citric acid and fatty alcohol and/or mixed esters of fatty acids containing 6 to 22 carbon atoms, methyl glucose and polyols, preferably glycerol, and
(12) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. The products in question are w/o or o/w emulsifiers, depending on the degree of ethoxylation. Reaction products with 1 to 100 mol ethylene oxide are particularly suitable for the preparations according to the invention.

Polyolpoly-12-hydroxystearates and the mixtures thereof which are marketed under the names of "Dehymuls® PGPH" (w/o emulsifier) or "Eumulgin® VL 75" (mixture with Coco Glucosides in a ratio by weight of 1:1, o/w emulsifier) or Dehymuls® SBL (w/o emulsifier) by Cognis Deutschland GmbH) are also preferred for the purposes of the invention by virtue of their mildness. The polyol component of these emulsifiers may be derived from substances which contain at least 2, preferably 3 to 12 and more particularly 3 to 8 hydroxyl groups and 2 to 12 carbon atoms.

Suitable lipophilic w/o emulsifiers are, in principle, emulsifiers with an HLB value of 1 to 8 which are summarized in numerous tables and which are known to the expert. Some of these emulsifiers are listed, for example, in Kirk-Othmer, Encyclopedia of Chemical Technology, 3rd Edition, 1979, Vol. 8, page 913. For ethoxylated products, the HLB value can be calculated using the following equation: $HLB=(100-L):5$, where L is the percentage by weight of the lipophilic groups, i.e. the fatty alkyl or fatty acyl groups, in % by weight in the ethylene oxide adducts.

Particularly advantageous w/o emulsifiers are partial esters of polyols, more particularly $C_{3-6}$ polyols such as, for example, glyceryl monoesters, partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

In cases where water-soluble active components and water are incorporated, at least one emulsifier from the group of nonionic o/w emulsifiers (HLB value: 8–18) and/or solubilizers should be used. Such emulsifiers and/or solubilizers are, for example, the ethylene oxide adducts mentioned at the beginning with a correspondingly high degree of ethoxylation, for example 10–20 ethylene oxide units for o/w emulsifiers and 20 to 40 ethylene oxide units for so-called solubilizers. According to the invention, Ceteareth-20 and PEG-20 Glyceryl Stearate are particularly advantageous o/w emulsifiers.

Nonionic emulsifiers from the group of alkyl oligoglycosides are particularly kind to the skin and, accordingly, are particularly suitable as o/w emulsifiers for the purposes of the invention. They enable the sensory properties of the compositions to be optimized and provide for particularly easy incorporation of the polycarbonates. $C_{8-22}$ alkyl mono- and oligoglycosides, their production and their use are known from the prior art. They are produced in particular by reacting glucose or oligosaccharides with primary alcohols containing 8 to 22 carbon atoms, preferably 12 to 22 and more particularly 12 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based. Products available under the name of Plantacare® contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the name of Emulgade® PL 68/50 by Cognis Deutschland GmbH, which is a 1:1 mixture of alkyl polyglucosides and fatty alcohols, is preferred for the purposes of the invention. The mixture of Lauryl Glucoside, Polyglyceryl-2-Dipolyhydroxystearate, glycerol and water which is marketed under the name of Eumulgin® VL 75 may also be used with advantage for the purposes of the invention.

A particularly preferred embodiment of the composition according to the invention contains:

(a) 1 to 10% by weight polycarbonates with an average molecular weight of 300 to 100,000,
(b) 5 to 30% by weight oil components,
(c) 0.1 to 10% by weight emulsifier(s),
(d) 0 to 90% by weight water.

Other Surfactants/emulsifiers

The compositions may also contain zwitterionic, amphoteric, cationic and anionic surfactants according to the application envisaged. The combination with selected anionic surfactants is particularly suitable for the purposes of the invention.

Zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is a particularly preferred zwitterionic surfactant.

Ampholytic surfactants are also suitable, particularly as co-surfactants. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylamino-butyric acids, N-alkyliminodipropionic acids, N-hydroxyethyl-N-alkyl-amidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the expert in large numbers from relevant textbooks and are commercially available. They are, in particular, alkyl sulfates in the form of their alkali metal, ammonium or alkanolammonium salts, alkylether sulfates, alkylether carboxylates, acylisethionates, acyl sarcosinates, acyl taurines containing linear $C_{12-18}$ alkyl or acyl groups and sulfosuccinates and acyl glutamates in the form of their alkali metal or ammonium salts. Among the anionic surfactants, alkali metal salts of fatty acids (sodium stearate) and, in particular, alkyl sulfates (Lanette® E) and alkyl phosphates (Amphisol® K) are particularly suitable for the preparations according to the invention because they lead to particularly stable and homogeneous emulsions with relatively high viscosities.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

Humectants/skin Moisturizers

In another preferred embodiment, the composition according to the invention also contains a humectant which contributes towards optimizing the sensory properties of the composition and which serves to regulate the skin moisture level. At the same time, the low-temperature stability of the preparations according to the invention, particularly in the case of emulsions, is increased. The humectants are normally present in a quantity of 0.11 to 15% by weight, preferably 1 to 10% by weight and more particularly 5 to 10% by weight.

According to the invention, suitable humectants are inter alia amino acids, pyrrolidone carboxylic acid, lactic acid and salts thereof, lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol and triglycerol.

UV Protection Factors and Antioxidants

A preferred embodiment of the preparations according to the invention relates to sun protection formulations, i.e. the preparations according to the invention additionally contain a UV filter. It has surprisingly been found that the polycarbonates improve the water resistance of sun protection formulations and thus provide long-time protection in water.

Since ca. 60% UV-B and ca. 80% UV-A radiation (based on the UV reaching the earth's surface) is still active in water to a depth of 50 cm, the water resistance of sun protection emulsions is particularly important, especially for children and aquatic athletes. Effective sun protection emulsions should be made water-resistant, should stay firmly on the skin and should only be slowly washed off in water. According to the COLIPA recommendations, a sun protection formulation is water-resistant if at least 50% of the original sun protection effect is still present after exposure to water under defined conditions. The sun protection effect is achieved by the use of suitable UV filters.

UV protection factors in the context of the invention are, for example, organic substances (light filters) which are liquid or crystalline at room temperature and which are capable of absorbing ultraviolet or infrared radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor as described in EP 0693471 B1;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives as described in EP 0694521 B1.

Suitable water-soluble substances are
- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione and the enamine compounds described in DE 197 12 033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SOFW-Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to 1mole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Deodorant and Antiperspirant Components

Another preferred embodiment of the composition according to the invention additionally contains a deodorizing/antiperspirant component or a combination of such components. The water resistance of the preparations is also of importance in this embodiment, ensuring that the active components are not washed off by perspiration and do not adhere to clothing.

Such active components include astringent metal salts (antiperspirant components), germ inhibitors, enzyme inhibitors, odor absorbers, odor maskers or combinations of these active components. The deodorant/antiperspirant components are present in the compositions according to the invention in a quantity of 0.1 to 30% by weight, preferably in a quantity of 5 to 25% by weight and more particularly in a quantity of 10 to 25% by weight (based on the quantity of active substance).

Suitable antiperspirant components are, for example, aluminium chlorhydrates, aluminium/zirconium chlorhydrates and zinc salts. These antiperspirants probably act by partially blocking the sweat glands through the precipitation of proteins and/or polysaccharides. Besides the chlorhydrates, aluminium hydroxylactates and acidic aluminium/zirconium salts may also be used. For example, an aluminium chlorhydrate which corresponds to the formula $[Al_2(OH)_5Cl]\cdot 2.5H_2O$ and which is particularly preferred for the purposes of the invention is commercially available under the name of Locron® from Clariant GmbH. The aluminium/zirconium tetrachlorohydrex/glycine complexes marketed, for example, by Reheis under the name of Rezal® 36G are also preferably used in accordance with the invention.

Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Cognis Deutschland GmbH). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in the compositions. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component.

Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Insect Repellents

Another preferred embodiment of the composition according to the invention contains an insect repellent or a combination of insect repellents. The water resistance of the preparations is also important for this embodiment, ensuring that the active components are not washed off and long-term protection is developed.

Suitable insect repellents are N,N-diethyl-m-toluamide, pentane-1,2-diol, 3-(N-n-butyl-N-acetylamino)-propionic acid ethyl ester), which is marketed as Insect Repellent 3535 by Merck KGaA, and Ethyl Butylacetyl-aminopropionate. They are normally used in the compositions according to the invention in a quantity of 0.1 to 10% by weight, preferably in a quantity of 1 to 8% by weight and more particularly in a quantity of 2 to 6% by weight, based on the overall composition.

Viscosity Adjusters

The required viscosity for the compositions according to the invention is achieved by addition of viscosity adjusters. Viscosity adjusters additionally increase the water resistance of the preparations according to the invention. Accordingly, a preferred embodiment of the preparation according to the invention additionally contains at least one viscosity adjuster. Suitable viscosity adjusters are inter alia consistency factors such as, for example, fatty alcohols or hydroxyfatty alcohols containing 12 to 22 and preferably 16 to 18 carbon atoms and also partial glycerides, fatty acids containing 12 to 22 carbon atoms or 12-hydroxyfatty acids. A combination of these substances with alkyl oligoglucosides and/or fatty acid N-methyl glucamides of the same chain length and/or polyglycerol poly-12-hydroxystearates is preferably used because combinations such as these provide particularly stable and homogeneous emulsions. Other suitable viscosity adjusters are thickeners such as, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), uncrosslinked and polyol-crosslinked polyacrylic acids, polyacrylamides, polyvinyl alcohol and polyvinyl pyrrolidone. Other viscosity adjusters which have proved to be particularly effective are bentonites, for example Bentone®) Gel VS-5PC (Rheox) which is a mixture of cyclopentasiloxane, Disteardimonium Hectorite and propylene carbonate. Other suitable viscosity adjusters are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable viscosity adjusters also include anionic, zwitterionic, amphoteric and nonionic copolymers such as, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, acrylamidopropyl trimethylammonium chloride/acrylate copolymers, octylacrylamide/methyl methacrylate/tert.-butylaminoethyl methacrylate/2-hydroxypropyl methacrylate copolymers, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil., 108, 95 (1993).

According to the invention, it is preferred to use polymers in quantities of 0.1 to 5% by weight, preferably in quantities of 0.1 to 3% by weight and more particularly in quantities of 0.1 to 2% by weight, based on the composition as a whole. Polyacrylic acid homopolymers and copolymers are particularly preferred for the purposes of the invention because the resulting preparations according to the invention undergo little or no change in viscosity, even during long-term storage at elevated temperatures.

Other Auxiliaries and Additives (Optional)

The compositions according to the invention may contain other auxiliaries and additives according to the particular application envisaged, including for example fats and waxes, pearlizing waxes, superfatting agents, stabilizers, cationic, zwitterionic or amphoteric polymers, biogenic agents, film formers, swelling agents, hydrotropes, preservatives, antidandruff agents, self-tanning agents, solubilizers, perfume oils, dyes, etc. which are mentioned by way of example in the following.

Fats and waxes in the context of the invention are understood to be any lipids of fat- or wax-like consistency which have a melting point above 20° C. These include, for example, the standard triacyl glycerols, i.e. the triple esters of fatty acids with glycerol which may be of vegetable or animal origin. They may also be mixed esters, i.e. triple esters of glycerol with various fatty acids, or mixtures of various glycerides, including mixtures of mono-, di- and triglycerides. So-called hardened fats and oils obtained by partial hydrogenation are also particularly suitable for the purposes of the invention. Vegetable hardened fats and oils are preferred, for example hardened castor oil, peanut oil, soybean oil, rape oil, rapeseed oil, cotton-seed oil, sunflower oil, palm oil, palm kernel oil, linseed oil, almond oil, corn oil, olive oil, sesame oil, cocoa butter and coconut oil. Oxidation-stable vegetable glycerides commercially available as Cegesoft® and Novata® are particularly suitable.

Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and micro-waxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Besides the fats, other suitable additives are fat-like substances, such as lecithins and phospholipids. Lecithins are glycerophospholipids which are formed from fatty acids, glycerol, phosphoric acid and choline by esterification and are also frequently referred to as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates). Sphingosines and sphingolipids are also suitable as fat-like substances.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially Lauron®; distearylether; fatty acids, such as stearic acid, $C_{12-22}$ hydroxyfatty acids, behenic acid, ring opening products of $C_{12-22}$ olefin epoxides with $C_{12-22}$ fatty alcohols and/or polyols containing 2 to 15 carbon atoms and 2 to 10 hydroxyl groups and mixtures thereof.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Metal salts of fatty acids such as, for example, magnesium, aluminium and/or zinc stearate or ricinoleate may be used as stabilizers.

Suitable cationic polymers, which further optimize the sensory profile of the compositions according to the invention and give the skin a feeling of softness, are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®) L, Grunau), quaternized wheat poly-peptides, polyethyleneimine, cationic silicone polymers such as, for example, Amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quatemized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable silicone compounds were mentioned above in connection with the oil components. Besides dimethyl polysiloxanes, methylphenyl polysiloxanes and cyclic silicones, other suitable silicone compounds are amino-, fatty acid-, alcohol-, polyether-, epoxy-, fluorine-, glycoside- and/or alkyl-modified silicone compounds which may be both liquid and resin-like at room temperature,. Other suitable silicone compounds are simethicones which are mixtures of dimethicones with an average chain length of 200 to 300 dimethylsiloxane units and silicon dioxide or hydrogenated silicates.

Biogenic agents suitable for the purposes of the invention are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes. Active components such as these are used as radical traps in sun protection formulations and serve to regenerate the skin.

So-called film formers, which lead to a further improvement in the sensory profile of the preparations according to the invention, are, for example, chitosan, microcrystalline chitosan, quaternized chitosan, collagen, hyaluronic acid and salts thereof and similar compounds and the polyvinyl pyrrolidones, vinyl pyrrolidone/vinyl acetate copolymers, polymers of the acrylic acid series and quaternary cellulose derivatives.

Suitable antidandruff agents are Pirocton Olamin (1-hydroxy4-methyl-6-(2,4,4-trimethylpentyl)-2-(1H)-pyridinone monoethanolamine salt), Baypival® (Climbazole), Ketoconazol® (4-acetyl-1 -{4-[2-(2,4-dichlorophenyl) r-2-(1H-imidazol-1-ylmethyl)-1,3-dioxylan-c-4-ylmethoxy-phe-nyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

A suitable self-tanning agent is, for example, dihydroxyacetone. Suitable tyrosinase inhibitors, which prevent the formation of melanin and are used in depigmenting agents, are, for example, arbutin, ferulic acid, koji acid, coumaric acid and ascorbic acid (vitamin C).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipenta-erythritol;

short-chain alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Suitable preservatives are, for example, phenoxyethanol, formal-dehyde solution, parabens, pentanediol or sorbic acid and the silver complexes known under the name of Surfacine® and the other classes of compounds listed in Appendix 6, Parts A and B of the Kosmetik-verordnung ("Cosmetics Directive").

Suitable perfume oils are natural, vegetable and animal and also synthetic perfumes or mixtures thereof. Natural perfumes are obtained inter alia by extraction of flowers, stems and leaves, fruits, fruit peel, roots and resins of plants. Animal raw materials, for example civet and beaver, may also be used. Typical synthetic perfume compounds are products of the ester, ether, aldehyde, ketone, alcohol and hydrocarbon type. Mixtures of various perfumes, which together produce an attractive perfume note, are preferably used.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106.

The total percentage content of auxiliaries and additives may be from 1 to 50% by weight and is preferably from 5 to 40% by weight, based on the preparations according to the invention. The preparations according to the invention may be produced by standard hot or cold processes and are preferably produced by the phase inversion temperature method.

EXAMPLES

The polycarbonates are synthesized in accordance with WO 00/01755 where a detailed description of the reaction can be found. A general production process and the components to be used and the quantities in which they are used are described in the following. The reaction may be carried out with dimethyl or diethyl carbonate. The following Examples relate to the reaction with dimethyl carbonate.

General Synthesis Procedure

An initial molecular weight of diol to dimethyl carbonate of 1:1.0 to 1:1.5 is normally selected for the synthesis of the polycarbonates. The crude products obtained were analyzed and the OH value (OHV) or the average molecular weight were determined. In a second step, more diol was added and the esterification was continued to adjust the OH value and the viscosity to the required values: OH value ca. 50–60, viscosity: ca. 5,000–35,000 mPa·s (Brookfield RVF, 25° C., spindle according to viscosity, as recommended by the manufacturer). The OH value can be converted into the average molecular weight using the following equation: MW=functionality·56110/OH value (DGF-Methode: DGF C-V 17 a or DIN 53 240, Q-C 1220.0, Methoden der Analyse in der Chemie, Vol. 4, page 322).

The diol was introduced into the reactor and dried in vacuo (1–5 mbar) at 120 to 140° C. After addition of the catalyst (tetrabutyl orthotitanate), dimethyl carbonate was slowly added against a gentle stream of nitrogen and the methanol formed by the reaction at that temperature (T=120° C.) was continuously distilled off. A heatable column or a heated (50–60° C.) ascending condenser was placed in between to separate methanol from unreacted dimethyl carbonate. The vapor temperature (bridge head temperature) was regulated to 63–65° C. through the addition rate of the dimethyl carbonate. After all the dimethyl carbonate had been added (3 to 4 h), the reactor temperature was kept at 140° C. for 0.5 h, after which the azeotrope of dimethyl carbonate/methanol was distilled off at 200° C. After the vapor temperature had fallen distinctly, vacuum was applied (10 mbar) and the remaining dimethyl carbonate was distilled off. To complete the reaction and to react off the nonsymmetrical methyl carbonate formed in a secondary reaction, the reaction mixture was vigorously stirred at 200° C. for ca. 0.5 to 1 h after a vacuum of <15 mbar had been reached. The reaction mixture was then purged with nitrogen and a sample was taken to determine the OH value and viscosity.

Since the reaction had been calculated to give too low an OH value (ca. 10 to 20 units lower), the corresponding quantity of diol was then added (such calculations are familiar to the expert) and the esterification was continued for 0.5 h at 200° C. to achieve the required specifications. To deactivate the catalyst, 5% phosphoric acid was added over a period of 1 h at 100° C. and the reaction mixture was dried in vacuo. Cloudy, colorless to pale yellow liquids were obtained. The viscosities of polycarbonates I–V were determined with a Brookfield viscosimeter (Brookfield, RVF, spindle 5, 10 r.p.m., 23° C.).

Polycarbonate I (Sovermol ® 913/1) based on dimer diol 908:

| | |
|---|---|
| Sovermol ® 908 [dimer diol] OHV = 205 | 246.3 kg (450 mol) |
| dimethyl carbonate [Enichem] | 48.6 kg (540 mol) |
| Sovermol ® 908 [dimer diol] subsequently added | 10 kg |
| tetrabutyl orthotitanate | 0.295 kg (0.87 mol) |
| 5% phosphoric acid | 1.7 kg (0.87 mol) |

Product data polycarbonate I:

OH value: 55, acid value: 0.2, viscosity: ca. 30,000 mPa·s

Polycarbonate II based on Pripol ® 2033:

| | |
|---|---|
| Pripol ® 2033 [dimer diol] OHV = 205 | 947 g (1.73 mol) |
| dimethyl carbonate [Enichem] | 187 g (2.08 mol) |
| Pripol ® 2033 [dimer diol] subsequently added | 39 g |
| tetrabutyl orthotitanate (0.1%) | 1.13 g (3.32 mol) |
| 5% phosphoric acid | 6.51 g (3.32 mol) |

Product data polycarbonate II:

OH value: 56, acid value: ≦0.5, viscosity: ca. 30,000 mPa·s

Polycarbonate III based on dimer diol ® 908:

| | |
|---|---|
| Sovermol ® 908 [dimer diol] OHV = 209 | 2685 g (4 mol) |
| dimethyl carbonate [Enichem] | 473 g (5.25 mol) |
| Sovermol ® 908 [dimer diol] subsequently added | 482 g |
| tetrabutyl orthotitanate (0.1%) | 3.2 g (9.4 mMol) |
| 5% phosphoric acid | 18.5 g (9.4 mMol) |

Product data polycarbonate III:

OH value: 80, acid value: 0.3, viscosity: ca. 16,000 mPa·s

Polycarbonate IV based on dimer diol ® 908:

| | |
|---|---|
| Sovermol ® 908 [dimer diol] OHV = 206 | 2724 g (5 mol) |
| dimethyl carbonate [Enichem] | 495 g (5.5 mol) |
| Sovermol ® 908 [dimer diol] subsequently added | 1681 g |
| tetrabutyl orthotitanate (0.1%) | 3.26 g (9.6 mMol) |
| 5% phosphoric acid | 18.8 g (9.6 mMol) |

Product data polycarbonate IV:

OH value: 110, acid value: 0.3, viscosity: ca. 8,000 mPa·s

Polycarbonate V (Sovermol ® 920) based on Poly-THF:

| | |
|---|---|
| Poly-THF; OH value = 453 | 496 g (2 mol) |
| dimethyl carbonate [Enichem] | 227 g (2.52 mol) |
| Poly-THF subsequently added | — |
| tetrabutyl orthotitanate (0.1%) | 0.7 g (0.2 mol) |
| 5% phosphoric acid | 4 g (0.2 mol) |

Product data polycarbonate V:

OH value: 57, acid value: 0.2, viscosity: ca. 9,000 mPa·s

| Polycarbonate VI based on decane-1,10-diol: | |
|---|---|
| Decane-1, 10-diol, OHV = 635 | 1202 g (6.8 mol) |
| dimethyl carbonate [Enichem] | 858 g (9.52 mol) |
| Decane-1, 10-diol subsequently added | 58.4 g |
| tetrabutyl orthotitanate (0.1%) | 2 g (0.6 mol) |
| 5% phosphoric acid | 11.5 g (0.6 mol) |
| Product data polycarbonate VI: | |
| OH value: 56, acid value: 0.3, solidus point: 60° C. | |

| Polycarbonate VII based on dodecane-1,12-diol: | |
|---|---|
| Dodecane-1, 12-diol, OHV = 635 | 304 g (1.5 mol) |
| dimethyl carbonate [Enichem] | 190 g (2.1 mol) |
| Dodecane-1, 12-diol subsequently added | 22 g |
| tetrabutyl orthotitanate (0.1%) | 0.5 g (0.15 mol) |
| 5% phosphoric acid | 2.8 g (0.15 mol) |
| Product data polycarbonate VII: | |
| OH value: 56, acid value: 0.5, solidus point: 67° C. | |

Polycarbonate VIII based on hexane-1,6-diol:
Commercial product: Ravecarb® 106, MW: 2000, OH value: 56, viscosity>40,000 mPa·s.

Polycarbonate IX Based on a Mixture of pentane-1,5-diol and hexane-1,6-diol:
Commercial product: Ravecarb® 107, MW: 1850, OH value: 60, viscosity>40,000 mPa·s.

The polycarbonates were incorporated in basic formulations and the water resistance of the preparations according to the invention was determined. To determine the water resistance of the preparations according to the invention, a defined quantity of the preparations (cf. Table 1) was applied to a suitable carrier material and was "watered" to predetermined criteria in a glass beaker, the water being agitated by a magnetic stirrer. The SPF (sun protection factor) was determined before and after the treatment with water using a UV 1000S Labsphere Ultraviolet Transmittance Analyzer.

The sensory evaluation was conducted by a panel of ten trained volunteers who awarded scores of (1)=very good to (6)=unsatisfactory. The results represent the mean values of three measurements.

Water Resistance
  carrier material: Vitro-Skin N19, manuf.: IMS (4×3 cm) on slide frame
  quantity applied: 2 mg/cm$^2$
  drying time before 1st measurement: 15 ins., temp. 30° C.
  water temperature: 23° C. (16° d)
  pH value water: 7.0±0.5
  water volume: 400 ml
  stirring speed: 300 r.p.m. (magnetic stirrer)
  watering time: 2×20 mins. with an interval of 20 mins.
  drying time before 2nd measurement: 15 mins., temp. 30° C.

The results are set out in Tables 1a and 1b. Examples 1 to 6 (Table 1a) and 8 to 10 (Table 1b) correspond to the invention; Examples C1 and C2 are intended for comparison. Unless otherwise indicated, the quantities mentioned in the following Examples represent % by weight of the commercially available substances in the composition as a whole.

TABLE 1a

Basic formulations of sun porotection formulations; water resistance and sensory profile

| Composition/Performance | 1 | 2 | 3 | 4 | 5 | 6 |
|---|---|---|---|---|---|---|
| Eumulgin ® VL 75 | 4.0 | 4.0 | 4.0 | 4.0 | 4.0 | 4.0 |
| Myritol ® 331 | 7.0 | 7.0 | 7.0 | 7.0 | 7.0 | 7.0 |
| Cetiol ® OE | 6.0 | 6.0 | 6.0 | 6.0 | 6.0 | 6.0 |
| Eutanol ® G 16 | 3.0 | 3.0 | 3.0 | 3.0 | 3.0 | 3.0 |
| Polycarbonate I | 4.0 | | | | | |
| Polycarbonate II | | 4.0 | | | | |
| Polycarbonate III | | | 4.0 | | | |
| Polycarbonate IV | | | | 4.0 | | |
| Polycarbonate VIII (Ravecarb ® 106) | | | | | 4.0 | |
| Polycarbonate IX (Ravecarb ® 107) | | | | | | 4.0 |
| Neo Heliopan ® AV | 7.5 | 7.5 | 7.5 | 7.5 | 7.5 | 7.5 |
| Parsol ® 1789 | 2.0 | 2.0 | 2.0 | 2.0 | 2.0 | 2.0 |
| Carbopol ® 2984 | 0.2 | 0.2 | 0.2 | 0.2 | 0.2 | 0.2 |
| Glycerin | 5.0 | 5.0 | 5.0 | 5.0 | 5.0 | 5.0 |
| Water/NaOH/preservative | to 100/pH = 7/q.s | | | | | |
| In-vitro Sun Protection Factor (SPF) | | | | | | |
| Before treatment with water | 15 | 15 | 15 | 15 | 15 | 15 |
| After treatment with water | 14 | 14 | 14 | 13 | 12 | 12 |
| Difference (%-rel.) | 93 | 93 | 93 | 87 | 80 | 80 |
| Sensory evaluation | | | | | | |
| Absorption | 1 | 1 | 1 | 1 | 1 | 2 |
| Smoothness | 1 | 1 | 1 | 1 | 2 | 1 |
| +Tackiness | 1 | 1 | 1 | 1 | 1 | 1 |

TABLE 1b

Basic formulations of sun porotection formulations; water resistance and sensory profile

| Composition/Performance | 7 | 8 | 9 | 10 | C1 | C2 |
|---|---|---|---|---|---|---|
| Eumulgin ® VL 75 | 4.0 | 4.0 | 4.0 | 4.0 | 4.0 | 4.0 |
| Myritol ® 331 | 7.0 | 7.0 | 7.0 | 7.0 | 7.0 | 7.0 |
| Cetiol ® OE | 6.0 | 6.0 | 6.0 | 6.0 | 6.0 | 6.0 |
| Eutanol ® G 16 | 3.0 | 3.0 | 3.0 | 3.0 | 3.0 | 3.0 |
| Polycarbonate III | | | | 2.0 | — | — |
| Polycarbonate V | 4.0 | | | | | |
| Polycarbonate VI | | 4.0 | | | | |
| Polycarbonate VII | | | 4.0 | | | |
| Antaron ® V 220 | | | | 2.0 | 4.0 | |
| Antaron ® V 216 | | | | — | | 4.0 |
| Neo Heliopan ® AV | 7.5 | 7.5 | 7.5 | 7.5 | 7.5 | 7.5 |
| Parsol ® 1789 | 2.0 | 2.0 | 2.0 | 2.0 | 2.0 | 2.0 |
| Carbopol ® 2984 | 0.2 | 0.2 | 0.2 | 0.2 | 0.2 | 0.2 |
| Glycerin | 5.0 | 5.0 | 5.0 | 5.0 | 5.0 | 5.0 |
| Water, NaOH, preservative | to 100. pH = 7-q.s. | | | | | |
| In-vitro Sun-Protection-Factor (SPF) | | | | | | |
| Before treatment with water | 15 | 15 | 15 | 15 | 15 | 15 |
| After treatment with water | 13 | 12 | 13 | 13 | 9 | 10 |
| Difference (%-rel.) | 87 | 80 | 80 | 87 | 60 | 66 |
| Sensory evaluation | | | | | | |
| Absorption | 2 | 1 | 2 | 1 | 5 | 4 |
| Smoothness | 2 | 2 | 1 | 1 | 4 | 4 |
| Tackiness | 1 | 1 | 2 | 1 | 6 | 5 |

Comparison Examples C1 and C2, which contain Antaron® V220 and Antaron® V 216 instead of the polycarbonates, show distinctly reduced water resistance and are inferior in their sensory properties.

TABLE 2

O/W sunprotection emulsions

| Component | 11 | 12 | 13 | 14 | 15 | 16 | 17 | 18 | 19 | 20 | 21 |
|---|---|---|---|---|---|---|---|---|---|---|---|
| L = Lotion, C = Cream, S = Spray | L | C | S | L | C | L | L | C | L | C | L |
| Eumulgin ® VL 75 | | | | | | 4 | 4 | 2 | | | |
| Eumulgin ® B2 | 2 | | | | | | | | | | |
| Tween ® 60 | | | | 1 | | | | | | | |
| Myrj ® 51 | | 3 | | 2 | | | | | | | |
| Cutina ® E 24 | 1 | | | 1 | | | | | | | |
| Hostaphat ® KL 340 N | | | | | | | | | | 2 | |
| Lanette ® E | | | 0.5 | | | | | 0.5 | | | |
| Amphisol ® K | | | 1 | | 1 | | | 0.5 | | 1 | |
| Natriumstearat | | | | | | | 1 | | | | 2 |
| Emulgade ® PL 68/50 | | | 1 | | 5 | | | | | 4 | |
| Tego ® Care 450 | | | | | | | | | | 3 | |
| Cutina ® MD | 2 | | | 6 | | 4 | | | | 6 | |
| Lanette ® 14 | 1 | | | 1 | | | | 2 | | | 4 |
| Lanette ® O | 1 | 6 | | | 5 | 2 | | 2 | | | |
| Polycarbonate I and/or II and/or III and/or IV | 2 | 2 | 4 | 1 | 2 | 2 | 2 | 1 | 2 | 2 | 1 |
| Polycarbonate V | 0.5 | | | 1 | | | | 1 | | 0.5 | |
| Polycarbonate VI | 0.5 | | | 1 | | | | 1 | | 1 | |
| Polycarbonate VII | 1 | | | 1 | | | | 1 | | 0.5 | |
| Polycarbonate VIII | 1 | | | | | | | 0.5 | | 0.5 | |
| Polycarbonate IX | 1 | | | | | | | 0.5 | | 0.5 | |
| Emery ® 1780 | | | | | 0.5 | 0.5 | | | | | |
| Lanolin, anhydrous, USP | | | | | | | 5 | | | | |
| Myritol ® PC | | | | | 5 | | | | | | |
| Myritol ® 331 | 5 | | 8 | | 6 | | 10 | | 1 | 2 | |
| Finsolv ® TN | | | 1 | | | | | 1 | 8 | | |
| Cetiol ® CC | | 2 | 5 | | 4 | 4 | 2 | | | 2 | |
| Cetiol ® OE | | | 3 | | | | | | 2 | 3 | |
| Dow Corning DC ® 244 | 4 | | 1 | | 5 | | | 2 | | | 2 |
| Dow Corning DC ® 2502 | | 1 | | | 2 | | | | | | |

TABLE 2-continued

O/W sunprotection emulsions

| Component | 11 | 12 | 13 | 14 | 15 | 16 | 17 | 18 | 19 | 20 | 21 |
|---|---|---|---|---|---|---|---|---|---|---|---|
| Squatol ® S | | | | | | | 4 | | | | |
| Silikonöl Wacker AK ® 350 | | 2 | | | | | | | | | |
| Cetiol ® 868 | | | | | 2 | | 4 | | | | 7 |
| Cetiol ® J 600 | | | | | 3 | 2 | | | | 5 | |
| Mineral oil | | | | 9 | | | | | | | |
| Cetiol ® B | | | 1 | | | | | | | 2 | |
| Eutanol ® G | | | | | | | | | | | |
| Eutanol ® G 16 | | | | | | | | | | | |
| Cetiol ® PGL | | 5 | | | | | | | | 5 | |
| Almond oil | | | 2 | | | | 1 | | | | |
| Photonyl ® LS | | | | | 2 | | | | | 2 | |
| Panthenol | | | | | | 1 | | | | | |
| Bisabolol | | | | | | 0.2 | | | | | |
| Tocopherol/Tocopheryl acetate | | | | | | 1 | | | | | |
| Photonyl ® LS | | | | | | | | | | | |
| Neo Heliopan ® Hydro (Na salt) | 2 | | 2.2 | | 3 | 3 | | | | | 2 |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | 10 | 7 | |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® T 150 | 2 | | | | 2.5 | | | 1 | | | |
| Parsol ® 1789 | | 1 | 1 | | | | 2 | | 2 | 2 | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | | | 0.75 | | | | | 1 | 1 | | |
| Keltrol ® T | | | 0.25 | | | | | 0.5 | 0.5 | | |
| Carbopol ® 980 | | 0.5 | | 0.2 | 0.2 | 0.2 | | 0.5 | 0.1 | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH | | | | | | q.s. | | | | | |
| Water | | | | | | to 100 | | | | | |

Quantities represent % by weight of the commercially available substances in the composition as a whole.

TABLE 3

O/W sun protection emulsions

| Component | 22 | 23 | 24 | 25 | 26 | 27 | 28 | 29 | 30 | 31 | 32 |
|---|---|---|---|---|---|---|---|---|---|---|---|
| L = Lotion, | L | L | L | C | L | C | S | C | C | L | L |
| C = Cream, | | | | | | | | | | | |
| S = Spray | | | | | | | | | | | |
| Eumulgin ® VL 75 | 4 | 3 | 4.5 | | 3 | | | | 4 | | |
| Eumulgin ® B2 | | | | | | | | | | 1 | |
| Tween ® 60 | | | | | | | | | | 1 | |
| Myrj ® 51 | | | | | | | | | | | |
| Cutina ® E 24 | | | | 2 | | | | | | | |
| Hostaphat ® KL 340 N | | | | | | | | | | 0.5 | |
| Lanette ® E | 0.5 | | 0.5 | 0.5 | | | 0.1 | | 0.5 | | |
| Amphisol ® K | 0.5 | | | | | 1 | 1 | 1 | | | |
| Sodium stearate | | | | | 1 | | | | | | |
| Emulgade ® PL 68/50 | | 6 | | | | 4.5 | 1 | 5 | | | |
| Tego ® Care 450 | 1 | | | | | | | | 4 | | |
| Cutina ® MD | 1 | | | 8 | 6 | 1 | | | | 4 | 1 |
| Lanette ® 14 | | 2 | | | | | | 2 | | 1 | |
| Lanette ® O | | | | 2 | | | | | 1 | 1 | |
| Polycarbonate I and/or II and/or III and/or IV | 4 | 2 | 4 | 1 | 1 | 4 | 2 | 2 | 2 | 1 | 3 |
| Polycarbonate V | | | | | | | 0.5 | | | | 0.5 |
| Polycarbonate VI | | | | | | | 1 | | | 1 | 1.5 |
| Polycarbonate VII | | | | | | | 0.5 | | | | 0.5 |
| Polycarbonate VIII | | | | | | | 1 | | | | |
| Polycarbonate IX | | | | | | | 1 | | | 2 | |
| Emery ® 1780 | | | | | | | | | | | |
| Lanolin, anhydrous, USP | | | | | | | | | | | |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |

TABLE 3-continued

O/W sun protection emulsions

| Component | 22 | 23 | 24 | 25 | 26 | 27 | 28 | 29 | 30 | 31 | 32 |
|---|---|---|---|---|---|---|---|---|---|---|---|
| Cetiol ® CC | 6 |  | 6 |  |  | 5 | 5 |  |  |  |  |
| Cetiol ® OE |  |  |  |  | 2 |  |  |  |  |  | 2 |
| Dow Corning DC ® 244 |  | 2 |  |  | 1 |  |  |  |  |  |  |
| Dow Corning DC ® 2502 |  | 1 |  |  | 1 |  |  |  |  |  |  |
| Ceraphyl ® 45 |  |  |  |  |  |  |  |  |  | 2 | 2 |
| Silikonöl Wacker AK ® 350 |  |  |  |  | 1 |  |  |  |  |  |  |
| Cetiol ® 868 |  | 2 |  |  |  |  |  |  |  |  |  |
| Cetiol ® J 600 |  | 2 |  |  |  |  |  |  |  |  |  |
| Mineral oil |  |  |  | 10 |  |  |  |  |  |  |  |
| Cetiol ® B | 4 |  | 4 |  |  |  |  | 4 |  |  |  |
| Eutanol ® G |  | 3 |  |  |  | 3 |  |  |  |  |  |
| Eutanol ® G 16 S | 10 |  |  |  |  |  |  |  |  |  |  |
| Cetiol ® PGL |  |  |  |  |  |  |  |  | 2 |  |  |
| Photonyl ® LS |  |  |  |  |  |  |  |  |  | 2 |  |
| Panthenol |  |  |  |  |  | 1 |  |  |  |  |  |
| Bisabolol |  |  |  |  |  | 0.2 |  |  |  |  |  |
| Tocopherol/Tocopheryl acetate |  |  |  |  |  | 1 |  |  |  |  |  |
| Neo Heliopan ® Hydro (Na salt) |  |  |  |  |  |  |  |  |  | 3 |  |
| Eusolex ® OCR | 6 |  | 9 |  | 5 | 7 | 9 |  | 4 |  | 7 |
| Neo Heliopan ® BB |  |  |  |  |  |  |  | 1 | 1 |  | 1 |
| Neo Heliopan ® MBC |  | 2 |  | 1 |  |  |  | 3 | 1 |  | 3 |
| Neo Heliopan ® OS | 2 |  |  |  |  |  |  |  | 7 |  |  |
| Neo Heliopan ® E1000 |  | 4 |  |  |  |  |  | 5 |  |  |  |
| Neo Heliopan ® AV |  | 4 | 7.5 | 5 |  |  |  | 5 | 4 | 7.5 |  |
| Uvinul ® T 150 | 1 |  |  |  |  |  |  |  | 1.3 | 1 | 1 |
| Parsol ® 1789 | 1 |  |  |  |  |  |  |  | 2 |  | 1 |
| Z-Cote ® HP 1 | 7 | 2 | 5 |  |  | 7 | 5 |  | 6 | 2 |  |
| Eusolex ® T 2000 | 5 | 2 |  |  | 10 |  | 10 |  |  | 2 |  |
| Veegum ® Ultra | 1.5 |  | 1.5 |  | 1.5 | 1.2 |  | 1 |  |  |  |
| Keltrol ® T | 0.5 |  | 0.5 |  | 0.5 | 0.4 |  | 0.5 |  |  |  |
| Pemulen ® TR 2 |  | 0.3 |  | 0.3 |  |  | 0.1 | 0.2 |  |  | 0.3 |
| Ethanol |  | 5 |  | 8 |  |  |  |  |  |  |  |
| Butylene glycol | 1 |  |  | 3 | 3 |  |  |  |  | 8 | 1 |
| Glycerin | 2 | 4 | 3 | 3 |  | 3 | 3 | 3 | 5 |  | 3 |
| Water/preservative/NaOH |  |  |  |  | to 100/q.s./q.s |  |  |  |  |  |  |

Quantities represent % by weight of the commercially available substances in the composition as a whole.

TABLE 4

W/O sun protection emulsions

| Component | 33 | 34 | 35 | 36 | 37 | 38 | 39 | 40 | 41 | 42 | 43 |
|---|---|---|---|---|---|---|---|---|---|---|---|
| L = Lotion; C = Cream | C | L | C | L | C | L | L | L | L | C | C |
| Dehymuls ® PGPH | 4 | 2 | 1 | 3 | 3 | 1 | 1 | 2 | 2 | 4 | 1 |
| Monomuls ® 90-O18 |  |  | 2 |  |  |  |  |  |  |  |  |
| Lameform ® TGI | 2 |  | 4 |  | 3 |  |  |  |  | 1 | 3 |
| Abil ® EM 90 |  |  |  |  |  |  | 4 |  |  |  |  |
| Glucate ® DO |  |  |  |  |  |  |  |  |  |  | 3 |
| Isolan ® PDI |  |  |  |  |  | 4 |  | 2 |  |  |  |
| Arlacel ® 83 |  |  |  | 2 |  |  |  |  |  |  |  |
| Elfacos ® ST9 |  |  |  |  |  |  |  |  | 2 |  |  |
| Elfacos ® ST37 |  |  |  |  |  |  |  |  |  |  |  |
| Arlacel ® P 135 |  | 2 |  |  |  |  |  |  |  |  |  |
| Dehymuls ® HRE 7 |  |  |  |  |  |  |  |  |  |  |  |
| Zinc stearate |  | 1 |  | 1 | 1 |  |  | 1 |  | 1 |  |
| Microcrystalline wax |  |  | 5 |  |  | 2 |  |  |  |  | 5 |
| Beeswax |  | 1 |  | 1 |  |  |  | 5 |  | 7 |  |
| Tego ® Care CG |  |  |  |  | 1 |  |  |  |  |  | .5 |
| Prisorine ® 3505 |  | 1 |  | 1 | 1 |  | 1 | 1 |  |  | 1 |
| Polycarbonate I and/or II and/or III and/or IV | 3 | 4 | 2 | 1 | 1 | 2 | 2 | 2 | 3 | 1 | 1 |
| Polycarbonate V |  |  |  |  |  |  |  |  | 0.5 | 1 |  |
| Polycarbonate VI |  |  |  |  |  |  |  |  | 0.5 | 1 |  |
| Polycarbonate IV |  |  |  |  |  |  |  |  | 1 | 1 |  |
| Polycarbonate VIII |  |  |  |  |  |  |  |  | 0.5 |  |  |
| Polycarbonate IX |  | 2 |  |  |  |  |  |  |  |  |  |
| Emery ® 1780 |  |  | 5 |  |  |  |  |  |  | 4 |  |
| Wool wax alcohol, anhydrous, USP |  |  |  |  |  |  |  |  |  | 1 |  |
| Myritol ® PC |  |  |  |  | 3 |  | 4 |  |  |  |  |
| Myritol ® 331 |  | 10 |  |  | 3 | 6 |  |  |  | 8 |  |

TABLE 4-continued

W/O sun protection emulsions

| Component | 33 | 34 | 35 | 36 | 37 | 38 | 39 | 40 | 41 | 42 | 43 |
|---|---|---|---|---|---|---|---|---|---|---|---|
| Finsolv ® TN | | | | 5 | | | 5 | | | | |
| Cetiol ® CC | 12 | 22 | | | | 2 | | | 2 | | 5 |
| Cetiol ® OE | | | | | 4 | | 5 | | 4 | 2 | |
| Dow Corning DC ® 244 | | | | | | | 2 | | | | |
| Dow Corning DC ® 2502 | | | 1 | | 2 | | | | | | |
| Prisorine ® 3758 | | | | | | | | | | 2 | |
| Silikonöl Wacker AK ® 350 | | | | 4 | | | | 3 | | | |
| Cetiol ® 868 | | | | | | | | | | 2 | |
| Eutanol ® G 16 | | 3 | | | | | | | | | |
| Eutanol ® G 16S | | | | | | | | | | | |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G | | | 3 | | | | | 8 | | | |
| Cetiol ® PGL | | 11 | | | 4 | | | 9 | | | |
| Almond oil | | | | | 1 | 5 | | | | | |
| Photonyl ® LS | | | 2 | 1 | | | | | 4 | | |
| Panthenol | | | | | | 1.0 | | | | | |
| Bisabolol | | | | | | 0.2 | | | | | |
| Tocopherol/Tocopheryl acetate | | | | | | 1.0 | | | | | |
| Magnesium sulfate × 7 water | 1 | | | | | | | | | | |
| Neo Heliopan ® Hydro (Na salt) | | 2 | | 3 | | | | | | | |
| Neo Heliopan ® 303 | | | | | 4 | | | | | 6 | |
| Neo Heliopan ® BB | | 4 | 2 | | | | 2 | | | | |
| Neo Heliopan ® MBC | | | | | | | | 4 | | 3 | |
| Neo Heliopan ® OS | | | | | | | | | | | |
| Neo Heliopan ® E 1000 | | | | | | | | | 5 | | |
| Neo Heliopan ® AV | | 3 | 6 | 6 | | 7.5 | 7.5 | | 5 | | 7.5 |
| Uvinul ® T 150 | | | | | 2.5 | | | 1 | | 2 | |
| Parsol ® 1789 | | 2 | | | | | | 1 | | 2 | |
| Zinc oxide NDM | | | | | 6 | | | | | | |
| Eusolex ® T 2000 | 15 | | 10 | | 5 | | 4 | | | | 4 |
| Ethanol | | | | | | | | | | 8 | |
| Butylene glycol | | | 2 | 6 | | | 2 | 5 | | | 2 |
| Glycerin | 5 | 3 | 3 | | 5 | 3 | 2 | | 10 | 4 | |
| Water, preservative | | | | | to 100, q.s. | | | | | | |

Quantities represent % by weight of the commercially available substances in the composition as a whole.

TABLE 5

W/O sun protection emulsions

| Component | 44 | 45 | 46 | 47 | 48 | 49 | 50 | 51 | 52 | 53 | 54 |
|---|---|---|---|---|---|---|---|---|---|---|---|
| L = Lotion; C = Cream | L | C | L | L | C | L | L | L | L | C | C |
| Dehymuls ® PGPH | 3 | 1 | 5 | 1 | 1 | 3 | 2 | 4 | 0.5 | 1 | 4 |
| Monomuls ® 90-O18 | | 1 | | | | | | | | | |
| Lameform ® TGI | | | | | 4 | | | 1 | | 3 | 1 |
| Abil ® EM 90 | | | | 1 | | | | | 2 | | |
| Glucate ® DO | | | | 3 | | | | | 2 | | |
| Isolan ® PDI | | 3 | | | | | 4 | | | | |
| Arlacel ® 83 | | | | | | 3 | | | | | |
| Elfacos ® ST9 | | | | | | | | | | | 2 |
| Elfacos ® ST37 | 2 | | | | | | | | | | |
| Arlacel ® P 135 | | | | | | 3 | | | | | |
| Dehymuls ® HRE 7 | | | | | | | | | | 4 | |
| Zinc stearate | | | 2 | 2 | 1 | 1 | | | 1 | 1 | |
| Microcrystalline wax | | | | | 4 | | 1 | | | 4 | |
| Beeswax | | 4 | | 2 | | | 1 | | 2 | | 1 |
| Tego ® Care CG | | | | | | | | | | | |
| Isostearic acid | 1 | 1 | | | | | 1 | 1 | | 1 | 1 |
| Polycarbonate I and/or II and/or III and/or IV | 2 | 4 | 3 | 3 | 2 | 2 | 1 | 3 | 3 | 1 | 4 |
| Polycarbonate V | | 0.5 | | | | 1 | | | | | |
| Polycarbonate VI | | 0.5 | | | | | | | | | |
| Polycarbonate VII | | | | | | 0.5 | | | | | |
| Polycarbonate VIII | | | 2 | | | | | | | | |
| Polycarbonate IX | | 0.5 | | | | 1 | | | | | |

TABLE 5-continued

W/O sun protection emulsions

| Component | 44 | 45 | 46 | 47 | 48 | 49 | 50 | 51 | 52 | 53 | 54 |
|---|---|---|---|---|---|---|---|---|---|---|---|
| Emery ® 1780 | | 7 | 3 | | | | | | | | |
| Wool wax alcohol, anhydrous, USP | | | | | | | | | | | |
| Myritol ® PC | | | | | | | | | | | |
| Myritol ® 331 | 4 | 2 | 3 | | 5 | | | | 8 | 5 | 4 |
| Finsolv ® TN | | 5 | 5 | | | 7 | | | | | |
| Cetiol ® CC | 3 | 1 | | | | | 3 | 16 | | | 12 |
| Cetiol ® OE | | 3 | | 2 | | | 3 | | | | |
| Dow Corning DC ® 244 | | 4 | | 2 | | | | | | | |
| Dow Corning DC ® 2502 | | | | 1 | | | | | | | |
| Prisorine ® 3578 | | 1 | | | | | | | | | |
| Silikonöl Wacker AK ® 350 | | | | 1 | | | | | | | |
| Cetiol ® 868 | | | | | | | | | | | |
| Eutanol ® G 16 | | | | | | | | | | | 3 |
| Eutanol ® G 16S | | | | | | | | | | | 7 |
| Cetiol ® J 600 | | | | 3 | | | | | | | |
| Ceraphyl ® 45 | | | | 1 | | | | | 5 | 4 | |
| Mineral oil | | | | | | | 9 | | | | |
| Cetiol ® B | | | | | 3 | 3 | | | 2 | 2 | |
| Eutanol ® G | | | | 2 | | | | | | 5 | |
| Cetiol ® PGL | | | | | | | | | 2 | | |
| Almond oil | | | 2 | | | | | | | | |
| Photonyl ® LS | | | | | | | 3 | | | | 2 |
| Panthenol | | | | | | 1.0 | | | | | |
| Bisabolol | | | | | | 0.2 | | | | | |
| Tocopherol/Tocopheryl acetate | | | | | | 1.0 | | | | | |
| Magnesium sulfate × 7 water | | | | | | 1 | | | | | |
| Neo Heliopan ® Hydro (Na salt) | | 4 | | | | | | 4 | | | |
| Neo Heliopan ® 303 | 6 | 2 | | | | | | | 6 | | |
| Neo Heliopan ® BB | | 2 | | 2 | | 2 | | | | | |
| Neo Heliopan ® MBC | 2 | | | | 3 | | 4 | | 2 | | |
| Neo Heliopan ® OS | | | | | 10 | | 8 | | | | |
| Neo Heliopan ® E 1000 | | | 5 | 6 | | | | | | 5 | |
| Neo Heliopan ® AV | | 5 | 5 | | | 7.5 | | | | 5 | |
| Uvinul ® T 150 | 1 | | | 2 | 2 | | | | 3 | 2 | |
| Parsol ® 1789 | | 1 | 1 | | | | 1 | | 0.5 | | |
| Z-Cote ® HP 1 | 4 | 10 | | | | | | 5 | | | 5 |
| Titanium dioxide T 805 | | | 2 | | | 3 | | | 7 | 4 | 7 |
| Ethanol | | | | | 8 | 10 | | | | | |
| Butylene glycol | 5 | 1 | | 3 | 3 | | | | 8 | 2 | |
| Glycerin | | | 6 | 2 | | | 5 | 5 | | 3 | 5 |
| Water, preservative | | | | | | to 100, q.s. | | | | | |

Quantities represent % by weight of the commercially available substances in the composition as a whole.

TABLE 6

W/O care emulsions

| Component | 55 | 56 | 57 | 58 | 59 | 60 | 61 | 62 | 63 | 64 | 65 |
|---|---|---|---|---|---|---|---|---|---|---|---|
| L = Lotion. C = Cream | C | L | C | L | C | L | L | L | C | C | C |
| Polycarbonate I and/or II and/or III and/or IV | 1 | 1 | 2 | 1 | 1 | 1 | 1 | 1 | 2 | 2 | 1 |
| Polycarbonate V | | | | | 0.3 | | 0.3 | | | | |
| Polycarbonate VI | | | | | 0.3 | | 0.3 | | | | |
| Polycarbonate VII | | | | | 0.5 | | 0.5 | | | | |
| Polycarbonate VIII | | | | | 0.5 | | | | | | |
| Polycarbonate IX | 0.5 | | | | | 1 | | | 1 | | |
| Dehymuls ® PGPH | 1 | 3 | 1 | 2 | 3 | 1 | 1 | 2 | 1 | 1 | 1 |
| Monomuls ® 90-O18 | 2 | | | | | | | | 2 | | 2 |
| Lameform ® TGI | 4 | 1 | | | 3 | | | 1 | 4 | 3 | 3 |
| Abil ® EM 90 | | | | | | 4 | | | | | |
| Isolan ® PDI | | | | | 4 | | | | | | |
| Glucate ® DO | | | | 5 | | | | | | | |
| Arlacel ® 83 | | | 5 | | | | | | | | |
| Dehymuls ® FCE | | | | | | | | | | | |
| Dehymuls ® HRE 7 | | | | | | | | 4 | | 1 | |
| Zinc stearate | 2 | 1 | | 1 | 1 | | | 1 | 1 | 1 | |
| Microcrystalline wax | | 5 | | | 2 | | | | | 5 | |
| Beeswax | 4 | | | 1 | | | | 1 | 4 | 7 | |
| Tego Care ® CG | | | | | 1 | | | | | 0.5 | |

TABLE 6-continued

W/O care emulsions

| Component | 55 | 56 | 57 | 58 | 59 | 60 | 61 | 62 | 63 | 64 | 65 |
|---|---|---|---|---|---|---|---|---|---|---|---|
| Prisorine ® 3505 | | | 1 | 1 | | 1 | 1 | | | | 1 |
| Dry Flo ® Plus | | | | | | | | | | | |
| SFE 839 | | | | | | 3 | | | | | |
| Emery ® 1780 | 1 | | | | | | | | | | 1 |
| Lanolin; anhydrous USP | | | 5 | | | | | | | 4 | |
| Cegesoft ® C 17 | | | 3 | | | | | | | 1 | |
| Myritol ® PC | | | | | | 2 | | 4 | | | |
| Myritol ® 331 | | 6 | | | 2 | 6 | 2 | | | | 8 |
| Finsolv ® TN | | | | 5 | | 2 | 5 | | | | |
| Cetiol ® A | | | 6 | | | 4 | | | | | |
| Cetiol ® CC | | | 8 | | 2 | 2 | 2 | | | | 5 |
| Cetiol ® SN | | | 5 | | | | | | 3 | | |
| Cetiol ® OE | 3 | | | | 4 | | 2 | | 4 | 2 | |
| Dow Corning DC ® 244 | | | | | 1 | | 2 | | | | |
| Dow Corning DC ® 2502 | | | 1 | | 2 | | | | | | |
| Prisorine ® 3758 | | | | | 3 | | | | | | |
| Silikonöl Wacker AK ® 350 | | | | 4 | | | | 3 | | | |
| Cetiol ® 868 | | | | | | | | | | 2 | 7 |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | 8 | | | |
| Cetiol ® PGL | | | | | 4 | | | | 9 | | |
| Almond oil | | | | 1 | | 5 | | | | | |
| Insect Repellent ® 3535 | 2 | | | | | | | | | | |
| N,N-Diethyl-m-toluamide | | | | 3 | | | 5 | | | | |
| Photonyl ® LS | 2 | 2 | | | | | | | | | |
| Panthenol | | | | | 1.0 | | | | | | |
| Bisabolol | | | | | 0.2 | | | | | | |
| Tocopherol/Tocopheryl Acetate | | | | | 1.0 | | | | | | |
| Magnesium sulfate × 7 water | | | | | 1 | | | | | | |
| Bentone ® 38 | | | | 1 | | | | | | | |
| Propylene carbonate | | | | 0.5 | | | | | | | |
| Ethanol | | | | | | | | | 8 | | |
| Butylene Glycol | | | 2 | 6 | | | 2 | 5 | | | 2 |
| Glycerin | 5 | 3 | 3 | | 5 | 3 | 2 | | 10 | 4 | |
| Water, preservative | | | | | to 100, q.s. | | | | | | |

Quantities represent % by weight of the commercially available substances in the composition as a whole.

TABLE 7

W/O care emulsions

| Component | 66 | 67 | 68 | 69 | 70 | 71 | 72 | 73 | 74 | 75 | 76 |
|---|---|---|---|---|---|---|---|---|---|---|---|
| L = Lotion, C = Cream | L | C | L | L | C | L | L | L | L | C | C |
| Polycarbonate I and/or II and/or III and/or IV | 1 | 3 | 1 | 2 | 1 | 2 | 1 | 1 | 1 | 1 | 3 |
| Polycarbonate V | 0.5 | | | | | 0.5 | | | | | |
| Polycarbonate VI | 0.3 | | | | | 0.3 | | | | | |
| Polycarbonate VII | 0.3 | | | | | 0.3 | | | | | |
| Polycarbonate VIII | | | | | | | | | | | 0.2 |
| Polycarbonate IX | | | 1 | | | 0.2 | | | | | |
| Dehymuls ® PGPH | 3 | 1 | 5 | 1 | 1 | 3 | 3 | 4 | 1 | 1 | 1 |
| Monomuls ® 90-O18 | | 1 | | 1 | | | | | | | |
| Lameform ® TGI | | | | | 4 | | | 1 | | 3 | |
| Abil ® EM 90 | | | | 3 | | | | | | 2 | |
| Isolan ® PDI | | 3 | | | | | | | | | 4 |
| Glucate ® DO | 1 | | | | | | | | | | |
| Arlacel ® 83 | | | | | | 3 | | | | | |
| Dehymuls ® FCE | | | | | 4 | | 1 | | | | |
| Dehymuls ® HRE 7 | | | | | | | | | 7 | | |
| Zinc stearate | | 2 | 2 | 1 | 1 | | 1 | 1 | | | 1 |
| Microcrystalline wax | | | | | 4 | | 1 | | 4 | | |
| Beeswax | | 4 | 2 | | 2 | | 1 | 1 | 2 | | 5 |
| Tego ® Care CG | | | | | | | | | | | |
| Prisorine ® 3505 | 1 | 1 | | | | 1 | 1 | | | 1 | 1 |
| Dry Flo ® Plus | 1 | | | | | | | | | | |

TABLE 7-continued

W/O care emulsions

| Component | 66 | 67 | 68 | 69 | 70 | 71 | 72 | 73 | 74 | 75 | 76 |
|---|---|---|---|---|---|---|---|---|---|---|---|
| SFE ® 839 | | 5 | | | | 4 | | | | | |
| Emery ® 1780 | | | | | | | | | | | |
| Lanolin anhydrous USP | | 7 | 3 | | | | | | | | |
| Cegesoft ® C 17 | | | 2 | | | | | | | | |
| Myritol ® PC | | | | 8 | | | | | | | |
| Myritol ® 331 | 4 | | 3 | | 5 | 3 | | | 5 | 4 | |
| Finsolv ® TN | | | 5 | | | 7 | | | | | |
| Cetiol ® A | | | | | | | | 6 | | | |
| Cetiol ® CC | 3 | | | 6 | | 3 | 3 | | 8 | | |
| Cetiol ® SN | | | | | 5 | | | | | | |
| Cetiol ® OE | | | 3 | 2 | | | 3 | | | | 8 |
| Dow Corning ® DC 244 | | | 4 | 2 | | 2 | | | | | |
| Dow Corning ® DC 2502 | | | | 1 | | | | | | | |
| Prisorine ® 3758 | | | | | | 1 | | | | | |
| Silikonöl Wacker AK ® 350 | | | | 1 | | 1 | | 4 | | | |
| Cetiol ® 868 | | | | | | | | | | | 10 |
| Cetiol ® J 600 | 4 | | | 3 | | | | | | | |
| Ceraphyl ® 45 | | | | 1 | | | | | 5 | 4 | |
| Mineral oil | | | | | | | 9 | | | | |
| Cetiol ® B | | | | | 3 | 3 | | 2 | 2 | | |
| Eutanol ® G 16 | 1 | | | | | | | | | | |
| Eutanol ® G | | | | 2 | | | | | 5 | | |
| Cetiol ® PGL | | | 10 | | | | | 6 | | | 3 |
| Almond oil | | | 2 | | 5 | | 2 | | | | |
| Photonyl ® LS | | | | 2 | | | | | | | 2 |
| Panthenol | | | | | | 1.0 | | | | | |
| Bisabolol | | | | | | 0.2 | | | | | |
| Tocopherol/Tocopheryl acetate | | | | | | 1.0 | | | | | |
| Magnesium sulfate × 7 water | | | | | | 1 | | | | | |
| Bentone ® 38 | | | | | | 1 | | | | | |
| Propylene carbonate | | | | | | 0.5 | | | | | |
| Ethanol | | | | 8 | | 10 | | | | | |
| Butylene glycol | 5 | 1 | | 3 | 3 | | | | 8 | 2 | 1 |
| Glycerin | | | 6 | 2 | | | 5 | 5 | | 3 | 5 |
| Water, preservative | | | | | to 100, q.s. | | | | | | |

Quantities represent % by weight of the commercially available substances in the composition as a whole.

TABLE 8

O/W care emulsions

| Component | 77 | 78 | 79 | 80 | 81 | 82 | 83 | 84 | 85 | 86 | 87 |
|---|---|---|---|---|---|---|---|---|---|---|---|
| L = Lotion, C = Cream | C | C | C | L | C | L | L | C | L | C | C |
| Polycarbonate I and/or II and/or III and/or IV | 2 | 2 | 1 | 1 | 1 | 1 | 2 | 3 | 2 | 2 | 1 |
| Polycarbonate V | 0.3 | | | | | | | | | | |
| Polycarbonate VI | 0.3 | | | | | | | | | | |
| Polycarbonate VII | 0.3 | | | | | | | | | | |
| Polycarbonate VIII | | | | | | | | | | | 1 |
| Polycarbonate IX | | | | | | 1 | | | | | |
| Eumulgin ® VL 75 | | | | | | 4 | | | | | |
| Dehymuls ® PGPH | | 2 | | | | | | | | | |
| Generol ® R | | | 1 | | | | | | | | |
| Eumulgin ® B2 | | | 0.8 | | | | | | | | |
| Tween ® 60 | | | | 1 | | | | | | | |
| Cutina ® E 24 | | | 0.6 | 2 | | | | | | | |
| Hostaphat ® KL 340 N | | | | | | | | 2 | | | |
| Lanette ® E | | | | | | | | | 1 | | |
| Amphisol ® K | | 0.5 | | | | 1 | | | | 1 | 0.5 |
| Sodium stearate | | | | 0.5 | | | | | | | |
| Emulgade ® PL 68/50 | | 2.5 | | | | | | | | 4 | |
| Tego ® Care CG | | | | | | | | | | | 2 |
| Tego ® Care 450 | | | | | | | | 5 | | | |
| Cutina ® MD | | 1 | | 6 | 5 | | 4 | | | 6 | |
| Lanette ® 14 | | | 1 | | | | | 2 | | | 4 |
| Lanette ® O | 4.5 | | 4 | 1 | 2 | | | | | | 2 |
| Novata ® AB | | | 1 | | | | | | | | 1 |
| Emery ® 1780 | | | | | | 0.5 | 0.5 | | | | |

TABLE 8-continued

| Component | O/W care emulsions | | | | | | | | | | |
|---|---|---|---|---|---|---|---|---|---|---|---|
| | 77 | 78 | 79 | 80 | 81 | 82 | 83 | 84 | 85 | 86 | 87 |
| Lanolin, anhydrous, USP | | | | | | | 5 | | | | |
| Cetiol ® SB 45 | | | 1.5 | | | | 2 | | | | |
| Cegesoft ® C 17 | | | | | | | | | | | |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | |
| Cetiol ® CC | 4 | 6 | | | | 4 | 4 | | | | 5 |
| Cetiol ® OE | | | | | | | | | 4 | 3 | |
| Dow Corning DC ® 245 | | | 2 | | 5 | 1 | | | | | |
| Dow Corning DC ® 2502 | | | | | 2 | 1 | | | | | |
| Prisorine ® 3758 | | | | | | 1 | | | | | |
| Silikonöl Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | 5 | | | | | | | | |
| Cetiol ® B | | | | | | | | | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/Tocopheryl acetate | | | | | | | 1 | | | | |
| Veegum ® ultra | | | | | | | | | 1 | | |
| Keltrol ® T | | | 0.4 | | | | | | 0.5 | | |
| Pemulen ® TR 2 | 0.3 | | | | | | | 0.3 | | | |
| Carbopol ® Ultrez 10 | | 0.3 | 0.3 | 0.2 | 0.2 | 0.2 | | | 0.1 | 0.3 | 0.2 |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | | 4 | | 3 |
| Water, preservative, NaOH | | | | | | to 100, q.s., pH 6.5–7.5 | | | | | |

Quantities represent % by weight of the commercially available substances in the composition as a whole.

TABLE 9

| Component | O/W care emulsions | | | | | | | | | | |
|---|---|---|---|---|---|---|---|---|---|---|---|
| | 88 | 89 | 90 | 91 | 92 | 93 | 94 | 95 | 96 | 97 | 98 |
| L = Lotion, C = Cream | C | C | L | C | L | C | L | L | L | L | C |
| Polycarbonate I and/or II and/or III and/or IV | 2 | 3 | 1 | 2 | 1 | 2 | 1 | 1 | 1 | 1 | 3 |
| Polycarbonate V | 0.5 | | 0.5 | | | | | | | | 0.5 |
| Polycarbonate VI | 0.3 | | 0.3 | | | | | | | | 0.5 |
| Polycarbonate VII | 0.5 | | 0.5 | | | | | | | | 0.5 |
| Polycarbonate VIII | 0.2 | | | | | | | | | | 1 |
| Polycarbonate IX | | | | | | 1 | | | | | |
| Eumulgin ® VL 75 | 4 | 3 | | | | | 1 | | | | 2 |
| Generol ® R | | | | | | 2 | | | | | |
| Eumulgin ® B2 | | | | | | 2 | | | | 1 | |
| Tween ® 60 | | | | | | | | | | 1 | |
| Cutina ® E 24 | | | | 2 | | | | | | | |
| Hostaphat ® KL 340 N | | | | | | | | | | | |
| Lanette ® E | 0.5 | | | | | | | | | | 1 |
| Amphisol ® K | 0.5 | 1 | | | | | 1 | 1 | | | |
| Sodium stearate | | | | | 1 | | | | | | |
| Emulgade ® PL 68/50 | | 6 | | | | | 5 | | | 4 | |
| Tego ® Care CG | | | | | | | | | | | |
| Tego ® Care 450 | | | | | | | | 4 | | | |
| Cutina ® MD | 3 | | 3 | 8 | 6 | 8 | | | 4 | | |
| Lanette ® 14 | | 2 | | | | | 2 | | | 1 | |

TABLE 9-continued

O/W care emulsions

| Component | 88 | 89 | 90 | 91 | 92 | 93 | 94 | 95 | 96 | 97 | 98 |
|---|---|---|---|---|---|---|---|---|---|---|---|
| Lanette ® O | 2 |  |  | 2 |  | 3 | 1 |  | 1 | 1 | 6 |
| Novata ® AB |  |  |  |  |  |  |  |  |  |  |  |
| Emery ® 1780 |  |  |  |  |  |  |  |  |  |  |  |
| Lanolin, anhydrous, USP |  |  |  |  | 4 |  |  |  |  |  |  |
| Cetiol ® SB 45 |  |  |  |  |  | 2 |  |  |  |  |  |
| Cegesoft ® C 17 | 4 |  |  |  |  |  |  |  |  |  |  |
| Myritol ® PC | 6 |  |  |  |  | 5 |  | 5 |  |  |  |
| Myritol ® 331 | 5 |  | 5 |  |  | 7 |  |  |  | 10 | 3 |
| Finsolv ® TN |  | 5 |  |  | 5 |  |  | 3 | 3 |  | 1 |
| Cetiol ® CC |  |  |  |  |  |  |  |  |  |  | 2 |
| Cetiol ® OE |  |  |  | 2 |  | 2 |  | 5 |  |  |  |
| Dow Corning DC ® 245 |  | 2 |  | 1 |  |  |  |  |  | 8 | 2 |
| Dow Corning DC ® 2502 |  | 1 |  | 1 |  |  |  |  |  |  | 3 |
| Prisorine ® 3758 | 3 |  |  |  |  |  |  |  |  |  | 2 |
| Silikonöl Wacker AK ® 350 |  |  |  | 1 |  |  |  |  |  |  | 1 |
| Cetiol ® 868 |  | 2 |  |  |  |  |  |  |  |  |  |
| Cetiol ® J 600 |  | 2 |  |  |  |  |  |  |  |  |  |
| Ceraphyl ® 45 |  |  |  |  |  |  | 3 |  |  |  |  |
| Cetiol ® SN |  |  |  |  |  |  |  |  |  |  |  |
| Cetiol ® B |  |  | 5 |  |  | 5 | 4 |  |  |  | 3 |
| Eutanol ® G |  | 3 | 5 |  | 5 |  |  |  |  |  |  |
| Cetiol ® PGL |  |  |  |  |  |  |  | 5 | 2 |  |  |
| Dry Flo ® Plus |  | 1 |  |  |  |  |  |  |  |  | 1 |
| SFE 839 | 1 | 1 |  |  |  |  |  |  |  |  |  |
| Almond oil |  |  |  |  |  | 2 |  |  |  |  |  |
| Photonyl ® LS |  |  |  |  |  | 2 |  |  |  |  |  |
| Panthenol |  |  |  |  |  | 1 |  |  |  |  |  |
| Bisabolol |  |  |  |  |  | 0.2 |  |  |  |  |  |
| Tocopherol/Tocopheryl acetate |  |  |  |  |  | 1 |  |  |  |  |  |
| Veegum ® Ultra |  |  |  |  |  |  |  |  | 1 |  |  |
| Keltrol ® T |  |  |  |  |  |  |  |  | 0.5 |  |  |
| Carbopol ® ETD 2001 |  | 0.3 |  | 0.3 |  | 0.5 | 0.2 | 0.2 |  |  |  |
| Pemulen ® TR 2 |  |  | 0.3 |  |  | 0.3 |  |  |  |  | 0.5 |
| Ethanol |  | 5 |  | 8 |  |  |  |  |  |  | 10 |
| Butylene glycol | 5 |  | 2 | 3 | 3 |  |  |  |  | 8 |  |
| Glycerin | 2 | 4 | 3 | 3 |  | 7 | 5 | 3 | 5 |  |  |
| Water, preservative, NaOH |  |  |  |  | to 100, q.s. (pH 6.5–7.5) |  |  |  |  |  |  |

Quantities represent % by weight of the commercially available substances in the composition as a whole.

APPENDIX

1) Abil® EM 90
   INCI: Cetyl Dimethicone Copolyol
   Manufacturer: Tego Cosmetics (Goldschmidt)
2) Amphisol® K
   INCI: Potassium Cetyl Phosphate
   Manufacturer: Hoffmann La Roche
3) Antaron® V 220
   INCI: PVP/Eicosene Copolymer
   Manufacturer: GAF General Aniline Firm Corp. (IPS-Global)
4) Antaron® V 216
   INCI: PVP/Hexadecene Copolymer
   Manufacturer: GAF General Aniline Firm Corp. (IPS-Global)
5) Arlacel® 83
   INCI: Sorbitan Sesquioleate
   Manufacturer: Uniqema (ICl Surfactants)
6) Arlacel® P 135
   INCI: PEG-30 Dipolyhydroxystearate
   Manufacturer: Uniqema (ICl Surfactants)
7) Bentone® 38
   INCI: Quatemium-18 Hectorite
   Manufacturer: Rheox (Elementis Specialties)
8) Carbopol® 980
   INCI: Carbomer
   Manufacturer: Goodrich
9) Carbopol® 2984
   INCI: Carbomer
   Manufacturer: Goodrich
10) Carbopol® ETD 2001
    INCI: Carbomer
    Manufacturer: BF Goodrich
11) Carbopol® Ultrez 10
    INCI: Carbomer
    Manufacturer: Goodrich
12) Cegesoft® C 17
    INCI: Myristyl Lactate
    Manufacturer: Cognis Deutschland GmbH, Grünau
13) Ceraphyl® 45
    INCI: Diethylhexyl Malate
    Manufacturer: International Specialty Products
14) Cetiol® 868
    INCI: Ethylhexyl Stearate
    Manufacturer: Cognis Deutschland GmbH
15) Cetiol® A
    INCI: Hexyl Laurate
    Manufacturer: Cognis Deutschland GmbH 16) Cetiol® B
   INCI: Butyl Adipate
   Manufacturer: Cognis Deutschland GmbH (Henkel)
17) Cetiol® J 600
   INCI: Oleyl Erucate
   Manufacturer: Cognis Deutschland GmbH
18) Cetiol® OE
   INCI: Dicaprylyl Ether
   Manufacturer: Cognis Deutschland GmbH
19) Cetiol® PGL
   INCI: Hexyldecanol, Hexyldecyl Laurate
   Manufacturer: Cognis Deutschland GmbH
20) Cetiol® CC
   INCI: Dicaprylyl Carbonate
   Manufacturer: Cognis Deutschland GmbH
21) Cetiol® SB 45
   INCI: Shea Butter Butyrospermum Parkii (Linne)
   Manufacturer: Cognis Deutschland GmbH
22) Cetiol® SN
   INCI: Cetearyl Isononanoate
   Manufacturer: Cognis Deutschland GmbH (Henkel)
23) Cutina® E 24
   INCI: PEG-20 Glyceryl Stearate
   Manufacturer: Cognis Deutschland GmbH
24) Cutina® MD
   INCI: Glyceryl Stearate
   Manufacturer: Cognis Deutschland GmbH
25) Dehymuls® FCE
   INCI: Dicocoyl Pentaerythrityl Distearyl Citrate
   Manufacturer: Cognis Deutschland GmbH
26) Dehymuls® HRE 7
   INCI: PEG-7 Hydrogenated Castor Oil
   Manufacturer: Cognis Deutschland GmbH
27) Dehymuls® PGPH
   INCI: Polyglyceryl-2 Dipolyhydroxystearate
   Manufacturer: Cognis Deutschland GmbH
28) Dow Coming® 244 Fluid
   INCI: Cyclomethicone
   Manufacturer: Dow Coming
29) Dow Coming® 245 Fluid
   INCI: Cyclopentasiloxane Cyclomethicone
   Manufacturer: Dow Coming
30) Dow Coming® 2502
   INCI: Cetyl Dimethicone
   Manufacturer: Dow Corning
31) Dry®Flo Plus
   INCI: Aluminium Starch Octenylsuccinate
   Manufacturer: National Starch
32) Elfacos® ST 37
   INCI: PEG-22 Dodecyl Glycol Copolymer
   Manufacturer: Akzo-Nobel
33) Elfacos® ST 9
   INCI: PEG-45 Dodecyl Glycol Copolymer
   Manufacturer: Akzo-Nobel
34) Emery® 1780
   INCI: Lanolin Alcohol
   Manufacturer: Cognis Corporation (Emery)
35) Emulgade®PL 68/50
   INCI: Cetearyl Glucoside, Ceteayl Alcohol
   Manufacturer: Cognis Deutschland GmbH
36) Eumulgin® B 2
   INCI: Ceteareth-20
   Manufacturer: Cognis Deutschland GmbH
37) Eumulgin® VL 75
   INCI: Lauryl Glucoside (and) Polyglyceryl-2 Dipolyhydroxystearate (and) Glycerin
   Manufacturer: Cognis Deutschland GmbH
38) Eusolex® OCR
   INCI: Octocrylene
   Manufacturer: Merck
39) Eusolex® T 2000
   INCI: Titanium Dioxide, Alumina, Simethicone
   Manufacturer: Rona (Merck)
40) Eutanol® G
   INCI: Octyldodecanol
   Manufacturer: Cognis Deutschland GmbH
41) Eutanol®G 16
   INCI: Hexyldecanol
   Manufacturer: Cognis Deutschland GmbH
42) Eutanol®G 16 S
   INCI: Hexyldecyl Stearate
   Manufacturer: Cognis Deutschland GmbH
43) Finsolv® TN
   INCI: C 12/15 Alkyl Benzoate
   Manufacturer: Findex (Nordmann/Rassmann)
44) Generol® R
   INCI: Brassica Campestris (Rapseed) Sterols
   Manufacturer: Cognis Deutschland GmbH
45) Glucate® DO
   INCI: Methyl Glucose Dioleate
   Manufacturer: NRC Nordmann/Rassmann
46) Hostaphat® KL 340 N
   INCI: Trilaureth-4 Phosphate
   Manufacturer: Clariant
47) Isolan® PDI
   INCI: Diisostearoyl Polyglyceryl-3 Diisostearate
   Manufacturer: Goldschmidt AG
48) Keltrol® T
   INCI: Xanthan Gum
   Manufacturer: CP Kelco
49) Lameform® TGI
   INCI: Polyglyceryl-3 Diisostearate
   Manufacturer: Cognis Deutschland GmbH
50) Lanette® 14
   INCI: Myristyl Alcohol
   Manufacturer: Cognis Deutschland GmbH
51) Lanette® E
   INCI: Sodium Cetearyl Sulfate
   Manufacturer: Cognis Deutschland GmbH
52) Lanette® O
   INCI: Cetearyl Alcohol
   Manufacturer: Cognis Deutschland GmbH
53) Monomuls® 90-0-18
   INCI: Glyceryl Oleate
   Manufacturer: Cognis Deutschland GmbH
54) Myrj® 51
   INCI: PEG-30-Sterate
   Manufacturer: Uniqema
55) Myritol® 331
   INCI: Cocoglycerides
   Manufacturer: Cognis Deutschland GmbH
56) Myritol® PC
   INCI: Propylene Glycol Dicaprylate/Dicaprate
   Manufacturer: Cognis Deutschland GmbH
57) Neo Heliopan® 303
   INCI: Octocrylene
   Manufacturer: Haarmann & Reimer
58) Neo Heliopan® AV
   INCI: Ethylhexyl Methoxycinnamate
   Manufacturer: Haarmann & Reimer
59) Neo Heliopan® BB
   INCI: Benzophenone-3
   Manufacturer: Haarmann & Reimer 60) Neo Heliopan® E 1000
   INCI: Isoamyl-p-Methoxycinnamate
   Manufacturer: Haarmann & Reimer
61) Neo Heliopan® Hydro (Na-Salz)
   INCI: Phenylbenzimidazole Sulfonic Acid
   Manufacturer: Haarmann & Reimer
62) Neo Heliopan® MBC
   INCI: 4-Methylbenzylidene Camphor
   Manufacturer: Haarmann & Reimer
63) Neo Heliopan® OS
   INCI: Ethylhexyl Salicylate
   Manufacturer: Haarmann & Reimer
64) Novata® AB
   INCI: Cocoglycerides
   Manufacturer: Cognis Deutschland GmbH
65) Parsol® 1789
   INCI: Butyl Methoxydibenzoylmethane
   Manufacturer: Hoffmann-La Roche (Givaudan)
66) Pemulen® TR-2
   INCI: Acrylates/C10–30 Alkylacrylate Crosspolymer
   Manufacturer: Goodrich
67) Photonyl® LS
   INCI: Arginine, Disodium Adenosine Triphosphate, Mannitol, Pyridoxine HCL, Phenylalanine, Tyrosine
   Manufacturer: Laboratoires Serobiologiques (Cognis)
68) Pripol® 2033
   Dimer diol
   Manufacturer: Uniqema
69) Prisorine® ISAC 3505
   INCI: Isostearic Acid
   Manufacturer: Uniqema
70) Prisorine® 3758
   INCI: Hydrogenated Polyisobutene
   Manufacturer: Uniqema
71) Ravecarb® 106
   Polycarbonate diol
   Manufacturer: Enichem
72) Ravecarb® 107
   Polycarbonate diol
   Manufacturer: Enichem
73) SFE® 839
   INCI: Cyclopentasiloxane and Dimethicone/Vinyl Dimethicone Crosspolymer
   Manufacturer: GE Silicones
74) Silikonöl Wacker AK® 350
   INCI: Dimethicone
   Manufacturer: Wacker
75) Sovermol® 913/1
   Dimerdiol-908
   Manufacturer: Cognis Deutschland GmbH
76) Sovermol® 920
   Carbonic acid/polytetrahydrofuran polyester
   Manufacturer: Cognis Deutschland GmbH
77) Squatol® S
   INCI: Hydrogenated Polyisobutene
   Manufacturer: LCW (7-9 rue de l'Industrie 95310 St-Ouen l'Aumone France)
78) Tego® Care 450
   INCI: Polyglyceryl-3 Methylglucose Distearate
   Manufacturer: Tego Cosmetics (Goldschmidt)
79) Tego® Care CG 90
   INCI: Cetearyl Glucoside
   Manufacturer: Goldschmidt
80) Tween® 60
   INCI: Polysorbate 60
   Manufacturer: Uniqema (ICI Surfactants)
81) Uvinul® T 150
   INCI: Octyl Triazone
   Manufacturer: BASF
82) Veegum® Ultra
   INCI: Magnesium Aluminium Silicate
   Manufacturer: Vanderbilt
83) Z-Cote® HP 1
   INCI: Zinc Oxide, Dimethicone
   Manufacturer: BASF

The invention claimed is:

1. A cosmetic and/or pharmaceutical composition comprising:
   (a) a liquid to tacky polycarbonate, having a molecular weight of from 300 to 100,000, prepared by a process selected from the group consisting of polycondensation of diols and transesterification of diols selected from the group consisting of dimer diols, $\alpha,\omega$-pentane diols, $\alpha,\omega$-hexane diol and mixtures thereof;
   (b) an oil component;
   (c) optionally, an emulsifier; and
   (d) optionally, water, wherein, when applied to skin, water resistance of the composition is improved over a composition which does not contain the polycarbonate.

2. The composition of claim 1 wherein the polycarbonate is prepared by ransesterification of at least one diol with at least one member selected from the group consisting of dimethyl carbonate and diethyl carbonate.

3. The composition of claim 1 wherein the polycarbonate is prepared by transesterification between a hydrogenated dimer diol having an iodine value of from about 20 to 80 with at least one member selected from the group consisting of dimethyl carbonate and diethyl carbonate.

4. The composition of claim 1 wherein the polycarbonate is present in the composition in an amount of from about 0.1 to 20% by weight, based on the weight of the composition.

5. The composition of claim 1 wherein the polycarbonate is present in the composition in an amount of from about 1 to 10% by weight, based on the weight of the composition.

6. The composition of claim 1 wherein the oil component is present in the composition in an amount of from about 1 to 30% by weight, based on the weight of the composition.

7. The composition of claim 1 wherein the emulsifier is present in the composition in an amount of from about 0.1 to 15% by weight, based on the weight of the composition.

8. The composition of claim 1 wherein the emulsifier comprises an alkyl polyglycoside.

9. In a process for enhancing the water resistance of a cosmetic and/or pharmaceutical composition comprising at least one member selected from the group consisting of oil, emulsifiers, humectants, antioxidants, UV protection factors, viscosity adjuster, auxiliaries and additives; and optionally water, the improvement which comprises; introducing into the cosmetic and/or pharmaceutical composition a water resistance enhancing amount of a liquid to tacky polycarbonate, having a molecular weight of from 300 to 100,000, prepared by a process selected from the group consisting of polycondensation of diols and transesterification of diols selected from the group consisting of dimer diols, $\alpha,\omega$-pentane diols, $\alpha,\omega$-hexane diols and mixtures thereof.

10. The process of claim 9 wherein the polycarbonate is prepared by transesterification with at least one member selected from the group consisting of dimethyl carbonate and diethyl carbonate.

11. The process of claim 9 wherein the polycarbonate is prepared by the transesterification with at least one member selected from the group consisting of dimethyl carbonate and diethyl carbonate.

12. The process of claim 9 wherein the polycarbonate is prepared by the transesterification between a diol comprising a hydrogenated dimer diol having an iodine value of from about 20 to 80 with at least one member selected from the group consisting ofdimethyl carbonate and diethyl carbonate.

13. The process of claim 9 wherein the polycarbonate is present in the composition in an amount of from about 0.1 to 20% by weight, based on the weight of the composition.

14. The process of claim 9 wherein the polycarbonate is present in the composition in an amount of from about 1 to 10% by weight, based on the weight of the composition.

15. The process of claim 9 wherein the oil is present in the composition in an amount of from about 1 to 30% by weight, based on the weight of the composition.

16. The process of claim 9 wherein the emulsifier is present in the composition in an amount of from about 0.1 to 15% by weight, based on the weight of the composition.

17. The process of claim 9 wherein the emulsifier comprises an alkyl polyglycoside.

18. The composition of claim 1 comprising:
   (a) 1% to 10% by weight of the polycarbonate;
   (b) 5% to 30% by weight of the oil component;
   (c) 0.1% to 10% by weight of the emulsifier; and
   (d) 0 to 90% by weight of water.

19. The composition of claim 1 wherein the polycarbonate has a viscosity of 100 to 300,000 mPa·s at 23° C.

* * * * *